US00PP30354P3

(12) United States Plant Patent
Vinson

(10) Patent No.: US PP30,354 P3
(45) Date of Patent: Apr. 9, 2019

(54) ***FRAGARIA* PLANT NAMED 'SRV36'**

(50) Latin Name: ***Fragaria* x *ananassa***
Varietal Denomination: SRV36

(71) Applicant: Edward Vinson Limited, Faversham (GB)

(72) Inventor: Peter Edward Vinson, Faversham (GB)

(73) Assignee: EDWARD VINSON LIMITED, Faversham (GB)

( * ) Notice: Subject to any disclaimer, the term of this patent is extended or adjusted under 35 U.S.C. 154(b) by 0 days.

(21) Appl. No.: 15/732,155

(22) Filed: Sep. 26, 2017

(65) Prior Publication Data

US 2018/0098472 P1 Apr. 5, 2018

(30) Foreign Application Priority Data

Oct. 3, 2016 (QZ) ..... PBR 20162394

(51) Int. Cl.
*A01H 5/08* (2018.01)
*A01H 6/74* (2018.01)

(52) U.S. Cl.
USPC ..... Plt./208
CPC ..... *A01H 6/7409* (2018.05); *A01H 5/08* (2013.01)

(58) Field of Classification Search
USPC ..... Plt./208, 209
CPC ..... A01H 5/0893
See application file for complete search history.

*Primary Examiner* — Kent L Bell
(74) *Attorney, Agent, or Firm* — Penny J. Aguirre

(57) ABSTRACT

A new and distinct short day Mediterranean cultivar of strawberry plant named 'SRV36' that is characterized by its semi-upright, compact and moderately dense growth habit, its conical shaped berries that are uniformly large to medium in size, its berries with very firm skin and moderately juicy, firm flesh, its berries that are moderately to highly glossy and bright red in color, its vigorous growth with substantial fruit yield, its short day fruiting habit with early season production, its excellent tolerance to fruit skin damage caused by bruising, its slight to moderate petiole pubescence, and its tolerance to *Botryotinia cinerea* and slight susceptibility to *Podosphaera leucotricha* (powdery mildew).

2 Drawing Sheets

Botanical classification: *Fragaria* x *ananassa.*
Variety denomination: 'SRV36'.

BACKGROUND OF THE INVENTION

The present invention relates to a new and distinct cultivar of *Fragaria*, botanically known as *Fragaria* x *ananassa* 'SRV36', and will be referred to hereafter by its cultivar name, 'SRV36'. 'SRV36' is a Mediterranean short day strawberry primarily adapted to the climate and growing conditions of the Mediterranean and other regions of similar climate and day length.

The new cultivar was derived from an ongoing breeding program conducted by the Inventor at a farm in Cartaya, Huelva, Spain. 'SRV36' arose from a controlled cross made by the Inventor in 2012 between an unnamed selection from the Inventor's breeding program, designated as accession number SSD 02 as the female parent and an unnamed selection from the Inventor's breeding program, designated as accession number S06WL48 as the male parent. 'SRV36' was selected as a single unique plant in spring of 2013 from amongst the seedlings that resulted from the above cross.

Asexual reproduction of the new cultivar was first accomplished by rooting of stolons by the Inventor in Faversham, Kent, United Kingdom in 2013. Asexual propagation by rooting of stolons and tissue culture has shown that the unique characteristics of the new cultivar are stable and reproduced true to type in successive generations.

BRIEF SUMMARY OF THE INVENTION

The following traits have been repeatedly observed and represent the characteristics of the new cultivar. These attributes in combination distinguish 'SRV36' as a new and unique cultivar of *Fragaria.*

1. 'SRV36' exhibits a semi-upright growth habit.
2. 'SRV36' exhibits conical shaped berries that are uniformly large in size.
3. 'SRV36' exhibits berries with very firm skin and firm flesh.
4. 'SRV36' produces berries that contain high sugars, low acid levels and have mild-pleasant flavor.
5. 'SRV36' exhibits berries that are glossy and red in color with color retained throughout production.
6. 'SRV36' exhibits vigorous growth with substantial early fruit yields of marketable quality that is early medium in season.
7. 'SRV36' exhibits tolerance to *Botryotinia cinerea* and slight susceptibility to *Podosphaera leucotricha* (powdery mildew).

'SSD 02', the female parent of 'SRV36', differs from 'SRV36' in having berries that are not conical in shape, higher in acidity, and slightly darker red in color. 'S06WL48', the male parent of 'SRV36', differs from 'SRV36', in producing a moderate yield of smaller berries with outstanding flavor, soft skin and complex trusses. 'SRV36' can be most closely compared to the cultivar 'Viva Patricia' (U.S. Plant Pat. No. 22,717) with the following comparison characteristics observed under growing conditions in Spain. 'SRV36' produces comparable size fruit to 'Viva Patricia' and has a fruit shape that is less elongated than that of 'Viva Patricia', however 'SRV36' is more even in shape and has a considerably higher percentage of class 1 fruit. The fruit skin of 'SRV36' is similar in firmness to that of 'Viva Patricia', but the flesh is significantly firmer. 'SRV36' has a shorter flower truss length than that of 'Viva Patricia', and a mostly re-curved calyx position relative to the fruit. Furthermore, the fruit of 'SRV36' has a better shelf life and is less prone to infections by botrytis (*Botryotinia cinerea*) than that of 'Viva Patricia'.

'SRV36' plants exhibit a similarly vigorous growth habit to that of 'Viva Patricia', however when it is grown in Spain, the plant size of 'SRV36' is slightly smaller and not as dense as 'Viva Patricia'. The leaf size of 'SRV36' is medium, but significantly smaller than that of 'Viva Patricia'.

The petiole and petiolule lengths of 'SRV36' are slightly shorter than that of 'Viva Patricia'. Slight to moderate pubescence is present on 'SRV36' particularly at the base of the petiole and close to the stipules resulting in a similar density of pubescence to that of 'Viva Patricia'.

The leaflets of 'SRV36' typically possess an oblique and rounded base and rounded tip and the leaflets are generally asymmetrical. The leaflets of 'SRV36' express a distinctive architecture wherein the distance from the petiolule to the first serration is moderately longer on one side compared to the other. The leaf serrations are crenate. Plants of 'SRV36' possess a significantly higher number of serrations per leaf than that of 'Viva Patricia'. The most outstanding difference between the two varieties is expressed in the plant architecture; the plant habit of 'SRV36' is semi-upright and compact with mostly concave leaves, whereas the plant habit of 'Viva Patricia' is more spreading with the majority of leaves being flat to slightly concave. Many leaflets of 'SRV36' exhibit very weak or no puckering/blistering, similar to that of 'Viva Patricia'.

'SRV36' flower trusses tend to grow mostly above foliage, however a small percentage of trusses can be found within the leaf canopy, whereas the flowers trusses of 'Viva Patricia' are mainly even with the leaf canopy. All fruit trusses, when loaded with fruit, tend to protrude to the sides of the plant between the leaves rather than expressing a totally upward direction. The presence of a bract can be seen on almost all flower trusses and are small to medium in size.

The primary flowers of 'SRV36' are slightly smaller than those of 'Viva Patricia'. The flowers of 'SRV36' have fewer petals than those of 'Viva Patricia'. The calyx diameter of 'SRV36' is moderately smaller than that of 'Viva Patricia'. The calyxes of 'SRV36' are typically re-curving expressing a very narrow fruit neck at the top of the berry.

The glossiness of the berries of 'SRV36' are moderately high, the berries are medium to large in size with a shape that is predominantly conical. When grown in Spain, the fruit of 'SRV36' has an even, uniform shape without any white band around the neck, a feature that is prominent in the fruit of 'Viva Patricia', particularly in the early part of the season.

'SRV36' berries are slightly paler red than those of 'Viva Patricia'. During the cropping season, the fruit of 'SRV36' retains its bright red color and appears to be unaffected by the higher seasonal temperatures.

The achenes of 'SRV36' berries are characterized as being generally level with the surface of the fruit or slightly raised, compared to 'Viva Patricia' that features achenes that are generally even to slightly indented into the surface of the fruit. 'SRV36' berries generally contain slightly more achenes than those of 'Viva Patricia'.

The berries of 'SRV36' are noticeably firmer than those of 'Viva Patricia' throughout the cropping season with moderately high sugar and low acid levels. The berry skin of 'SRV36' is firmer than that of 'Viva Patricia' and resists bruising better during handling than the latter. The fruit flesh of 'SRV36' is firmer than that of 'Viva Patricia'.

BRIEF DESCRIPTION OF THE DRAWINGS

The accompanying colored photographs illustrate the overall appearance and distinct characteristics of the new cultivar. The photographs were taken of five month-old plants of 'SRV36' as grown outdoors in trial fields under polyethylene tunnels in Cartaya, Huelva, Spain.

Figure 1:
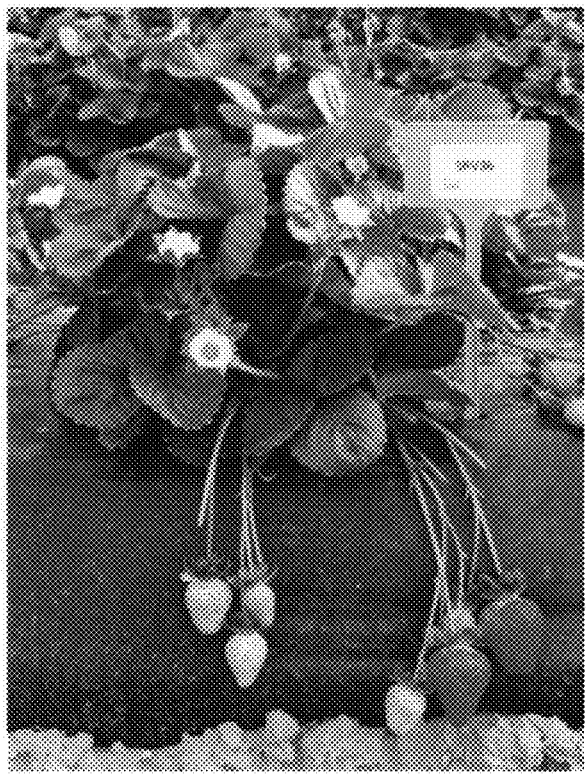
FIG. 1 provides a view of the compact moderately dense plant habit of 'SRV36' and fruit in various stages of development.
Figure 2:
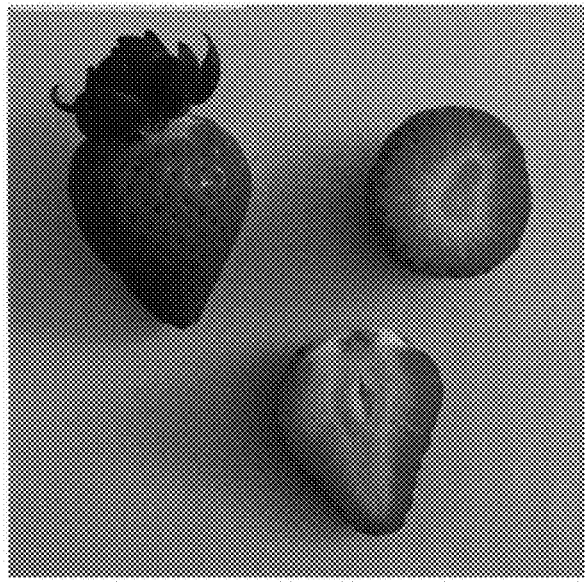
FIG. 2 provides a close-up view of the berry flesh and skin of 'SRV36'.
Figure 3:
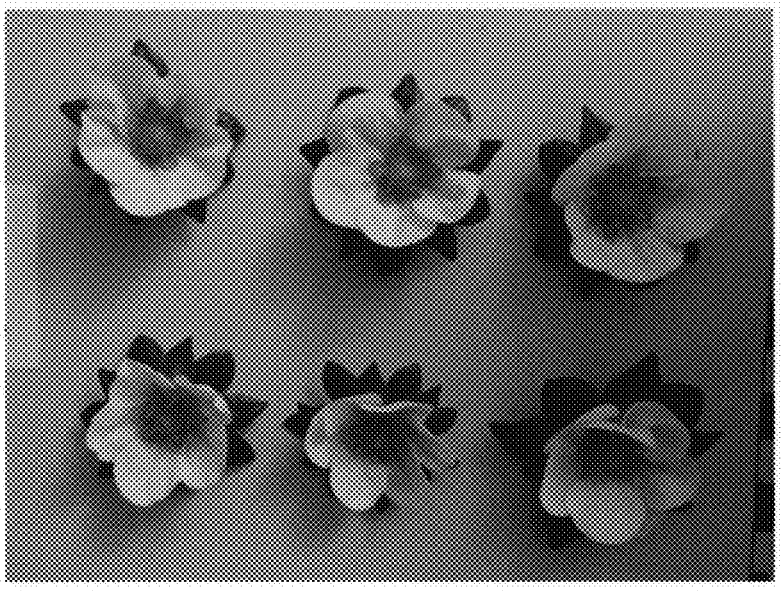
FIG. 3 provides a close-up view of the flowers of 'SRV36'.
Figure 4:
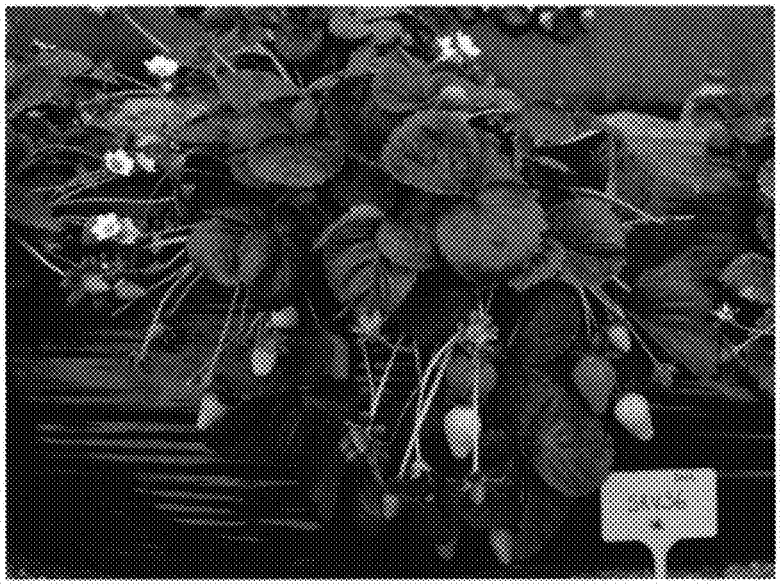
FIG. 4 provides a close-up view of a whole plant and fruit of 'SRV36' in mid-season.

The photographs depict color features as true as is reasonably possible with the digital photography methods used and the color values cited in the detailed botanical description accurately describe the new cultivar 'SRV36'.

DETAILED BOTANICAL DESCRIPTION

The following is a detailed description of five month-old plants of 'SRV36' as grown in trial fields with tunnels and polyethylene covers in Cartaya, Huelva, Spain. The phenotype of the new cultivar may vary with variations in environmental, climatic, and cultural conditions, as it has not been tested under all possible environmental conditions. The color determination is in accordance with The 1995 R.H.S. Colour Chart of The Royal Horticultural Society, London, England, except where general color terms of ordinary dictionary significance are used.

General description:

*Blooming period.*—Early-January through Mid-May in Cartaya, Huelva, Spain.

*Plant type.*—Herbaceous fruit producing perennial.

*Plant habit.*—Semi-upright, compact with medium dense canopy.

*Height and spread.*—Medium-large; reaches an average of 20 cm in height and 37 cm in width.

*Cold hardiness.*—Not tested in areas where temperatures of 32° F. occur.

*Diseases.*—Tolerance to *Botryotinia cinerea* and slight susceptibility to *Podosphaera leucotricha* (powdery mildew).

*Root description.*—Fibrous, white in color.

*Root development.*—An average of 2 weeks to initiate roots and 5 weeks to produce a young rooted plant.

*Propagation.*—Rooting of stolons and tissue culture.

*Growth rate.*—Vigorous.

*Stem description.*—Acaulescent, average of 4 crowns as a 5-month-old plant.

*Stolon description.*—Produced throughout the cropping season; 145A in color; surface pubescence is medium.

Foliage description:

*Leaf division.*—Three leaflets.

*Leaf arrangement.*—Basal.

*Leaf attachment.*—Petiolate.

*Leaflet shape.*—Rounded.

*Mid-tier leaflet size.*—Average of 6.9 cm in length and 6.8 cm in width.

*Leaflet margins.*—Crenate, an average of 34.9 serrations per leaf.

*Leaflet base.*—Asymmetrically oblique and rounded.

*Leaflet apex.*—Round.

*Leaflet glossiness.*—Upper surface medium, lower surface dull.

*Leaflet aspect.*—Most leaflets are slightly concave and overlapping.

*Leaflet interveinal blistering.*—Very weak.

*Leaflet venation.*—Pinnate, coloration matches leaflet color.

*Leaflet surface.*—Upper surface glabrous, lower surface very slightly pubescent, particularly along the vein, with very weak blistering depending on leaf age.

*Leaflet color.*—Upper surface 139A, lower surface 139C, no variegation present on either surface.

*Petiole.*—Round in shape, average of 14.3 cm in length and 0.4 cm in width, moderate to heavy pubescent surface (particularly heavy near base), up to 1 mm in length, 145A in color.

*Petiolules.*—Round in shape, average of 0.6 cm in length and 0.3 cm in width, moderately pubescent surface, 145A in color.

*Stipule.*—Average of 3.65 cm in length and 1.18 cm in width, moderate to strong anthocyanin 60A in color.

Flower description:

*Inflorescence.*—Truss.

*Inflorescence size.*—Medium to long in length, average of 26.1 cm.

*Flower initiation and expression conditions.*—Temperature and day-length dependent.

*Time of flowering* (50% *of plants at first flower*).—Early to mid-season.

*Flower position relative to foliage.*—Mostly above foliage with a few within the leaf canopy.

*Flower size.*—Average of 3.2 cm in diameter and 1.5 cm in height.

*Flower fragrance.*—Medium.

*Calyx.*—Average of 3.92 cm in diameter, larger than the corolla, mostly upwards, re-curved relative to fruit.

*Sepals.*—Average of 10.5, oblong to oblanceolate, 139A on upper surface, 139B on lower surface, obtuse base, acute apex, entire margin, almost no pubescence on upper surface and light pubescence on lower surface.

*Sepal position.*—Mixed arrangement relative to the fruit, most re-curving and some horizontal with fruit shoulder, however not touching the fruit.

*Petals.*—5-6 in number, average of 1.5 cm in length and 1.55 cm in width, rounded in shape, obtuse base and apex, overlapping, entire margins, upper and lower surface glabrous and 155C in color.

*Peduncle.*—145A in color, moderately pubescent surface, medium in strength, an average of 5 cm in length and 2.5 mm in width.

*Pedicel.*—145A in color, moderately pubescent surface, strong in strength, an average of 12 cm in length and 2 mm in width.

*Bracts.*—Observed on approximately 95% of the flower trusses from early developmental stage, which progresses into a small-medium single leaflet as the truss matures and fruit develops with characteristics similar to leaflets.

Reproductive organs:

*Gynoecium.*—Pistils; average of 140, average of 0.13 cm in length, steeply dome shaped, multiple simple pistils present, stigma; capitate shaped, 0.05 cm in length, style; average of 0.15 cm in length.

*Androecium.*—Stamens; average of 20, average of 2.3 mm in length, shape is a cone-like tube and wider at the base, anther; oval in shape, average of 1.7 mm in length, pollen; moderate in quantity and 7A in color.

Fruit description:

*Shape.*—Predominantly conical, shape is similar for primary, secondary and tertiary fruit.

*Season of harvest.*—End-January through Mid-May in Cartaya, Huelva, Spain.

*Time of ripening* (50% *of plants with first ripe fruit*).—Early.

*Type of bearing.*—Short day, Mediterranean.

*Size.*—Medium to large; an average of 5.46 cm in length and 4.26 cm in width.

*Surface.*—Smooth and medium to highly glossy.

*Calyx position.*—Even to very slightly lifted and mostly re-curved.

*Attitude of calyx segments.*—Mostly re-curved, very few touching the fruit shoulder, very strong adherence to the fruit.

*Diameter of calyx relative to fruit diameter.*—Significantly larger, later in season size is similar to fruit diameter.

*Glossiness.*—Even and medium-high.

*External color* (*skin*).—44A, color is retained throughout the cropping season and holds up well to high seasonal temperatures.

*Internal color* (*flesh*).—Near skin; 43A, near center; 36B.

*Evenness of color of skin.*—Very even.

*Evenness of color of flesh.*—Even, slightly paler near center.

*Acidity.*—Low.

*Sweetness.*—High.

*Soluble solids.*—8.7.

*Firmness.*—Skin is very firm (resistant to bruising), flesh is firm.

*Juiciness.*—Moderate.

*Brix.*—An average of 8.726° (average over 3 years of testing).

*Aroma.*—Slight.

*Weight.*—Average of 29.4 g per berry and 487 g per plant to end of March over three seasons in trials.

*Number of fruit per plant.*—Average 15 to end of March over three seasons in trials.

*Hollow center.*—Slight on primary fruit, weak or not present on secondary and tertiary fruit.

*Shelf life.*—An average of 8 to 10 days.

*Achene color.*—Yellow group 7A.

*Achene position.*—Even, level with the surface or slightly raised later in the season.

*Achene number.*—An average of 236 per berry.

*Band without achenes.*—Very narrow to none.

It is claimed:

1. A new and distinct cultivar of *Fragaria* plant named 'SRV36' as herein illustrated and described.

* * * * *